(12) United States Patent
Domash

(10) Patent No.: US 7,780,633 B2
(45) Date of Patent: Aug. 24, 2010

(54) SURGICAL CASSETTE WITH BUBBLE BREAKING STRUCTURE

(75) Inventor: David M. Domash, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 465 days.

(21) Appl. No.: 11/384,696

(22) Filed: Mar. 20, 2006

(65) Prior Publication Data

US 2007/0219493 A1    Sep. 20, 2007

(51) Int. Cl.
  *A61M 1/00*    (2006.01)
(52) U.S. Cl. .................................. 604/122
(58) Field of Classification Search .......... 604/122; 417/477.2
  See application file for complete search history.

(56) References Cited

U.S. PATENT DOCUMENTS

| | | |
|---|---|---|
| 3,683,913 A | 8/1972 | Kurtz et al. |
| 4,648,874 A * | 3/1987 | Kurtz et al. ............... 604/321 |
| 4,758,238 A | 7/1988 | Sundblom et al. |
| 5,041,096 A | 8/1991 | Beuchat et al. |
| 5,094,820 A * | 3/1992 | Maxwell et al. .......... 422/82.12 |
| 5,106,366 A | 4/1992 | Steppe |
| 5,267,956 A | 12/1993 | Beuchat |
| 5,364,342 A | 11/1994 | Beuchat et al. |
| 5,503,801 A * | 4/1996 | Brugger ....................... 422/44 |
| 5,582,601 A | 12/1996 | Wortrich et al. |
| 6,261,283 B1 | 7/2001 | Morgan et al. |
| 6,293,926 B1 | 9/2001 | Sorensen et al. |
| 6,561,999 B1 | 5/2003 | Nazarifar et al. |
| 6,572,349 B2 | 6/2003 | Sorensen et al. |
| 6,740,074 B2 | 5/2004 | Morgan et al. |
| 6,962,488 B2 | 11/2005 | Davis et al. |
| 2005/0040075 A1* | 2/2005 | Cerqueira et al. ........... 208/113 |
| 2005/0261619 A1* | 11/2005 | Gay .......................... 604/4.01 |

FOREIGN PATENT DOCUMENTS

GB    2166055 A    4/1986

* cited by examiner

*Primary Examiner*—Kevin C Sirmons
*Assistant Examiner*—Deanna K Hall
(74) *Attorney, Agent, or Firm*—W. David Lee

(57) ABSTRACT

A surgical cassette having a chamber for fluidly coupling to a source of vacuum in a surgical console and a bubble breaking structure disposed within the chamber. The cassette protects the source of vacuum from liquid.

1 Claim, 4 Drawing Sheets

SURGICAL CASSETTE WITH BUBBLE BREAKING STRUCTURE

FIELD OF THE INVENTION

The present invention generally pertains to a surgical cassette for use with microsurgical systems, and more particularly to such cassettes for use with ophthalmic microsurgical systems.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site. The types of aspiration systems used, prior to the present invention, were generally characterized as either flow controlled or vacuum controlled, depending upon the type of pump used in the system. Each type of system has certain advantages.

Vacuum controlled aspiration systems are operated by setting a desired vacuum level, which the system seeks to maintain. Flow rate is dependent on intraocular pressure, vacuum level, and resistance to flow in the fluid path. Actual flow rate information is unavailable. Vacuum controlled aspiration systems typically use a venturi or diaphragm pump. Vacuum controlled aspiration systems offer the advantages of quick response times, control of decreasing vacuum levels, and good fluidic performance while aspirating air, such as during an air/fluid exchange procedure. Disadvantages of such systems are the lack of flow information resulting in transient high flows during phacoemulsification or fragmentation coupled with a lack of occlusion detection. Vacuum controlled systems are difficult to operate in a flow controlled mode because of the problems of non-invasively measuring flow in real time.

Flow controlled aspiration systems are operated by setting a desired aspiration flow rate for the system to maintain. Flow controlled aspiration systems typically use a peristaltic, scroll, or vane pump. Flow controlled aspiration systems offer the advantages of stable flow rates and automatically increasing vacuum levels under occlusion. Disadvantages of such systems are relatively slow response times, undesired occlusion break responses when large compliant components are used, and vacuum can not be linearly decreased during tip occlusion. Flow controlled systems are difficult to operate in a vacuum controlled mode because time delays in measuring vacuum can cause instability in the control loop, reducing dynamic performance.

One currently available ophthalmic surgical system, the MILLENIUM system from Storz Instrument Company, contains both a vacuum controlled aspiration system (using a venturi pump) and a separate flow controlled aspiration system (using a scroll pump). The two pumps can not be used simultaneously, and each pump requires separate aspiration tubing and cassette.

Another currently available ophthalmic surgical system, the ACCURUS® system from Alcon Laboratories, Inc., contains both a venturi pump and a peristaltic pump that operate in series. The venturi pump aspirates material from the surgical site to a small collection chamber. The peristaltic pump pumps the aspirate from the small collection chamber to a larger collection bag. The peristaltic pump does not provide aspiration vacuum to the surgical site. Thus, the system operates as a vacuum controlled system.

In both vacuum controlled aspiration systems and flow controlled aspiration systems, the liquid infusion fluid and ophthalmic tissue aspirated from the surgical site are directed into an aspiration chamber within a surgical cassette. In vacuum controlled aspiration systems, the aspiration chamber in the surgical cassette is fluidly coupled to a source of vacuum within a surgical console. It is important to protect the source of vacuum from liquid, while maintaining the ability to aspirate air from above the partially liquid-filled aspiration chamber. In the past, hydrophobic filter media were incorporated into the fluid line between the vacuum source and aspiration chamber to provide such protection. However, such filter media delayed air flow and correspondingly increased the fluidic response time of the surgical system. In addition, large air chambers or long fluid paths have been incorporated into conventional ophthalmic surgical systems to reduce the likelihood of liquid reaching the source of vacuum. However, such added volumes of air increased the fluidic response time of the surgical system due to an increased amount of a compressible fluid in the system.

Accordingly, a need continues to exist for an improved method of protecting a source of vacuum in the aspiration system of a microsurgical system from liquid.

SUMMARY OF THE INVENTION

The present invention relates to a surgical cassette. The surgical cassette includes a chamber for fluidly coupling to a source of vacuum in a surgical console and for containing a volume of air, and a bubble breaking structure disposed within the chamber.

The volume of air comprises entrained liquid. The bubble breaking structure has a geometry that facilitates breaking of air bubbles so that the entrained liquid is removed from the air and does not pass to the source of vacuum.

BRIEF DESCRIPTION OF THE DRAWINGS

For a more complete understanding of the present invention, and for further objects and advantages thereof, reference is made to the following description taken in conjunction with the accompanying drawings, in which.

DETAILED DESCRIPTION OF THE PREFERRED EMBODIMENTS

Figure 1:
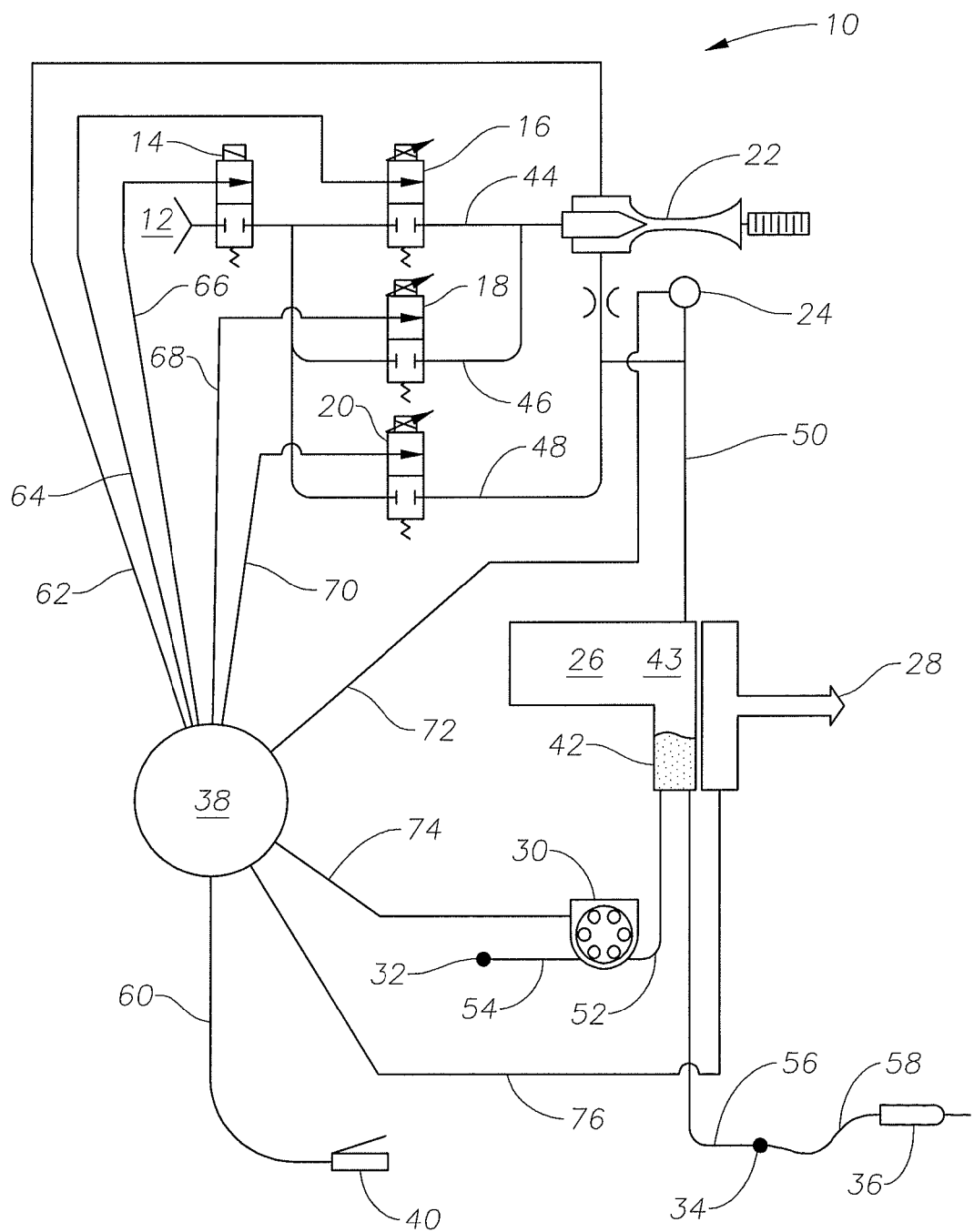
FIG. 1 is a schematic diagram illustrating aspiration control in a microsurgical system.

The preferred embodiments of the present invention and their advantages are best understood by referring to FIGS. 1-6 of the drawings, like numerals being used for like and corresponding parts of the various drawings.

Microsurgical system 10 includes a pressurized gas source 12, an isolation valve 14, a vacuum proportional valve 16, an optional second vacuum proportional valve 18, a pressure proportional valve 20, a vacuum generator 22, a pressure transducer 24, an aspiration chamber 26, a fluid level sensor 28, a pump 30, a collection bag 32, an aspiration port 34, a surgical device 36, a computer or microprocessor 38, and a proportional control device 40. The various components of system 10 are fluidly coupled via fluid lines 44, 46, 48, 50, 52, 54, 56, and 58. The various components of system 10 are electrically coupled via interfaces 60, 62, 64, 66, 68, 70, 72, 74, and 76. Valve 14 is preferably an "on/off" solenoid valve. Valves 16-20 are preferably proportional solenoid valves. Vacuum generator 22 may be any suitable device for generating vacuum but is preferably a vacuum chip or a venturi chip that generates vacuum when isolation valve 14 and vacuum proportional valves 16 and/or 18 are open and gas from pressurized gas source 12 is passed through vacuum generator 22. Pressure transducer 24 may be any suitable device for directly or indirectly measuring pressure and vacuum. Fluid level sensor 28 may be any suitable device for measuring the level of a fluid 42 within aspiration chamber 26 but is preferably capable of measuring fluid levels in a continuous manner. Pump 30 may be any suitable device for generating vacuum but is preferably a peristaltic pump, a scroll pump, or a vane pump. Microprocessor 38 is capable of implementing feedback control, and preferably PID control. Proportional controller 40 may be any suitable device for proportionally controlling system 10 and/or surgical device 36 but is preferably a foot controller.

System 10 preferably utilizes three distinct methods of controlling aspiration, vacuum control, suction control, and flow control. These methods are more fully described in co-pending U.S. application Ser. No. 11/158,238 filed Jun. 21, 2005 and co-pending U.S. application Ser. No. 11/158,259, both of which are commonly owned with the subject application and are incorporated herein by reference.

In each of these methods, vacuum may be provided to surgical device 36 and aspiration chamber 26 via fluid lines 50, 56, and 58. Aspiration chamber 26 fills with fluid 42 aspirated by surgical device 36. Fluid 42 includes liquid infusion fluid as well as aspirated ophthalmic tissue.

Figure 2:
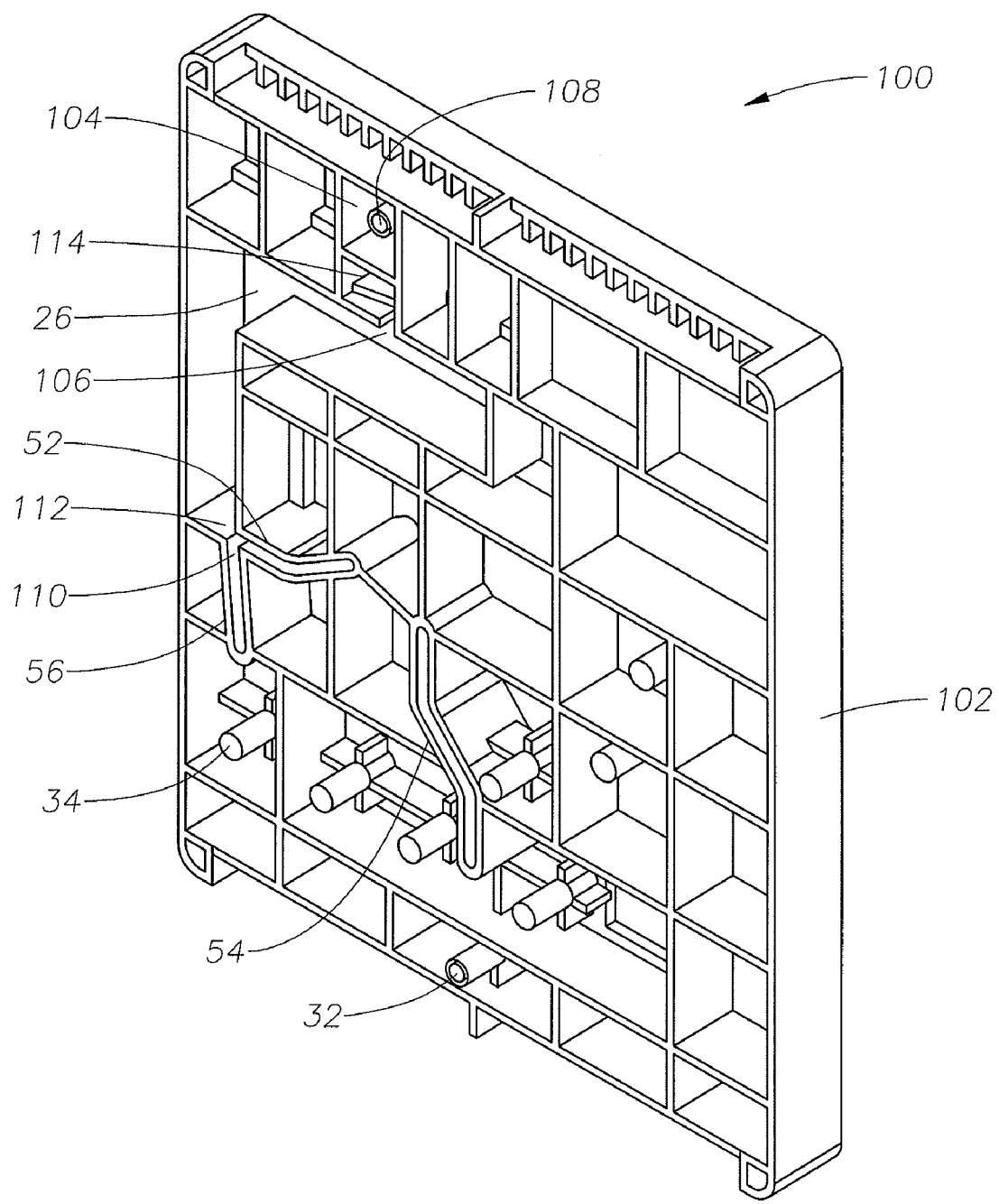
FIG. 2 is a front, perspective view of a body of a surgical cassette showing a bubble breaking structure according to a preferred embodiment of the present invention.
Figure 4:
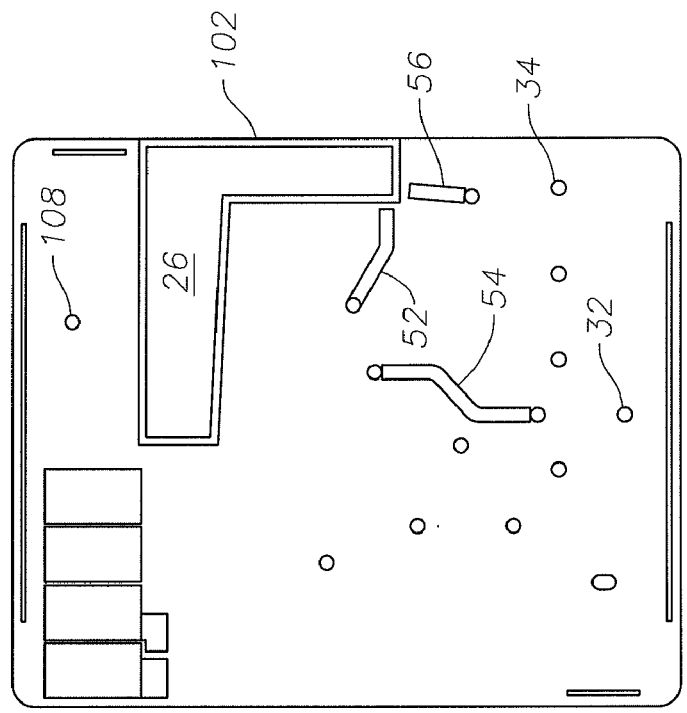
FIG. 4 is a rear view of the surgical cassette body of FIG. 2.
Figure 3:
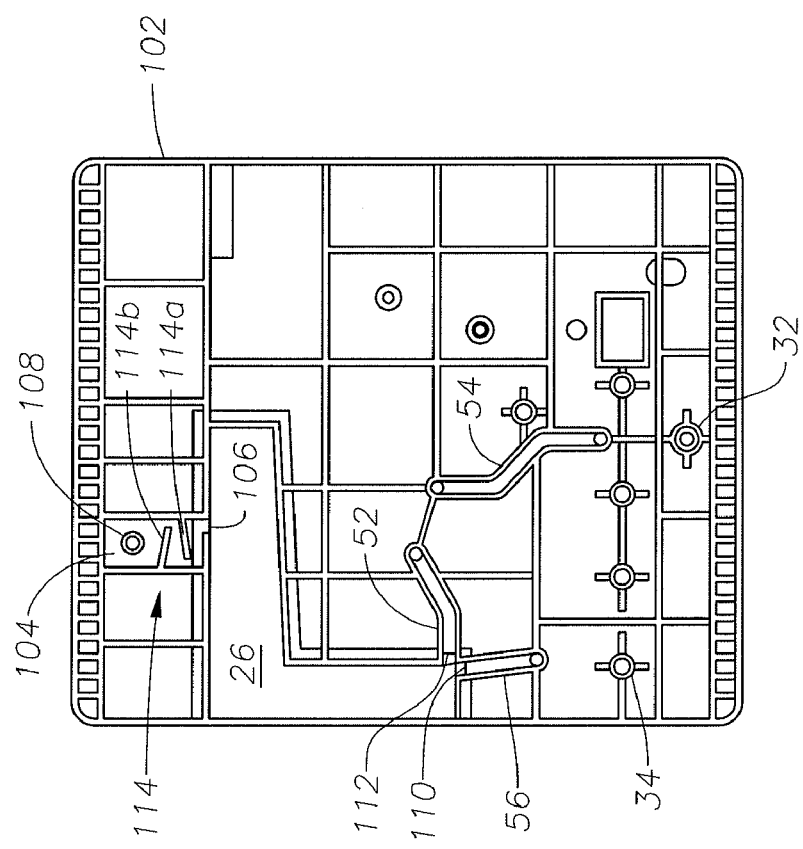
FIG. 3 is a front view of the surgical cassette body of FIG. 2.

As shown best in FIGS. 2-4, a surgical cassette 100 has a body 102 including aspiration chamber 26 and aspiration source chamber 104. A cover, which is fluidly sealed to the front side of body 102, is not shown for purposes of clarity. A pinch plate, which is fluidly sealed to the rear side of body 102, is not shown for purposes of clarity. Aspiration source chamber 104 preferably has a small volume relative to aspiration chamber 26. An entry 106 fluidly couples aspiration chamber 26 and aspiration source chamber 104. A port 108 fluidly couples aspiration source chamber 104 and fluid line 50. As discussed hereinabove, fluid line 50 is fluidly coupled to vacuum generator 22. An entry 110 fluidly couples aspiration chamber 26 and fluid line 56. An entry 112 fluidly couples aspiration chamber 26 and fluid line 52. Aspiration source chamber 104 includes a bubble breaking structure 114. Bubble breaking structure 114 preferably includes a first appendage 114a extending from an internal wall of aspiration source chamber 104 and a second appendage 114b extending from an internal wall of aspiration source 104. Appendages 114a and 114b preferably have a thin, planar geometry and are preferably disposed in an opposing manner relative to one another. The distal ends of appendages 114a and 114b are preferably angled downward toward aspiration chamber 26. Body 102 is preferably molded from a plastic material. Aspiration chamber 26, aspiration source chamber 104, entry 106, port 108, entry 110, entry 112, and bubble breaking structure 114 are preferably integrally molded into body 102.

As shown best in FIG. 1, liquid 42 is present in aspiration chamber 26, and air 43 is present in aspiration chamber 26 above liquid 42. When the surgical system supplies vacuum to aspiration chamber 26, some liquid 42 is mixed with air 43, typically on or in air bubbles, and is aspirated through entry 106 into aspiration source chamber 104. As such bubbles pass through entry 106, they contact appendage 114a, appendage 114b, and/or the internal surface of aspiration source chamber 104. Such contact breaks the bubbles, and any entrained liquid falls back into aspiration chamber 26 via entry 106. The downward angling of appendages 114a and 114b facilitates the flow of liquid back into aspiration chamber 26.

Figure 5:
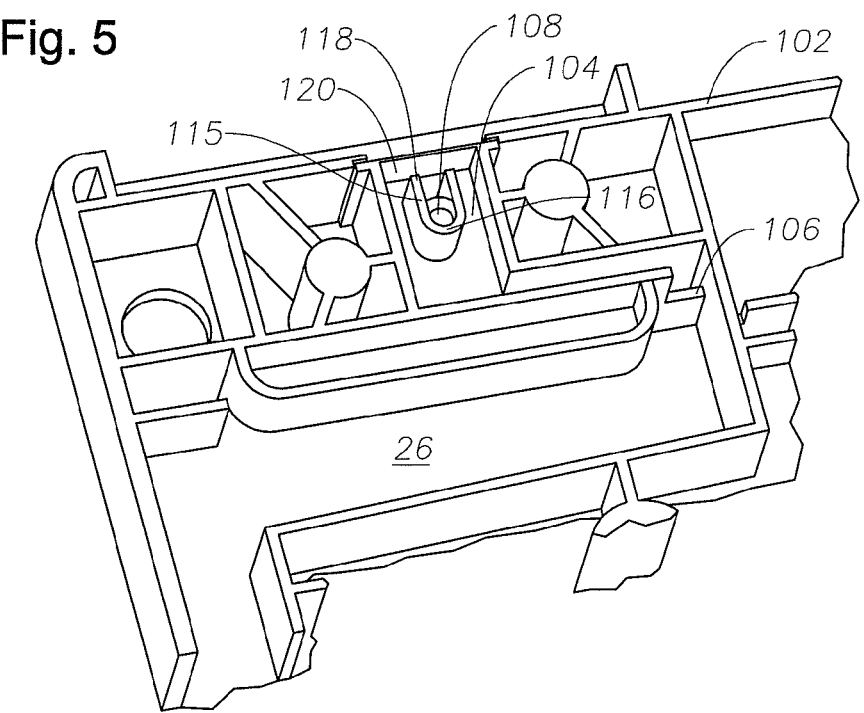
FIG. 5 is an enlarged, fragmentary, front, perspective view of body of a surgical cassette showing a bubble breaking structure according to a second preferred embodiment of the present invention.

FIG. 5 shows a bubble breaking structure 115 according to a second preferred embodiment of the present invention. Bubble breaking structure 115 includes a body 116 that shields port 108 from bubbles or other entrained liquid in aspiration source chamber 104. Body 116 preferably has a generally U-shaped geometry. Body 116 has an upper end 118 disposed just below internal wall 120 of aspiration source chamber 104 which allows passage of air into port 108. As bubbles pass around bubble breaking structure 115 toward upper end 118, they contact the internal surface of aspiration source chamber 104 and/or bubble breaking structure 115. Such contact breaks the bubbles, and any entrained liquid falls back into aspiration chamber 26 via entry 106.

Figure 6:
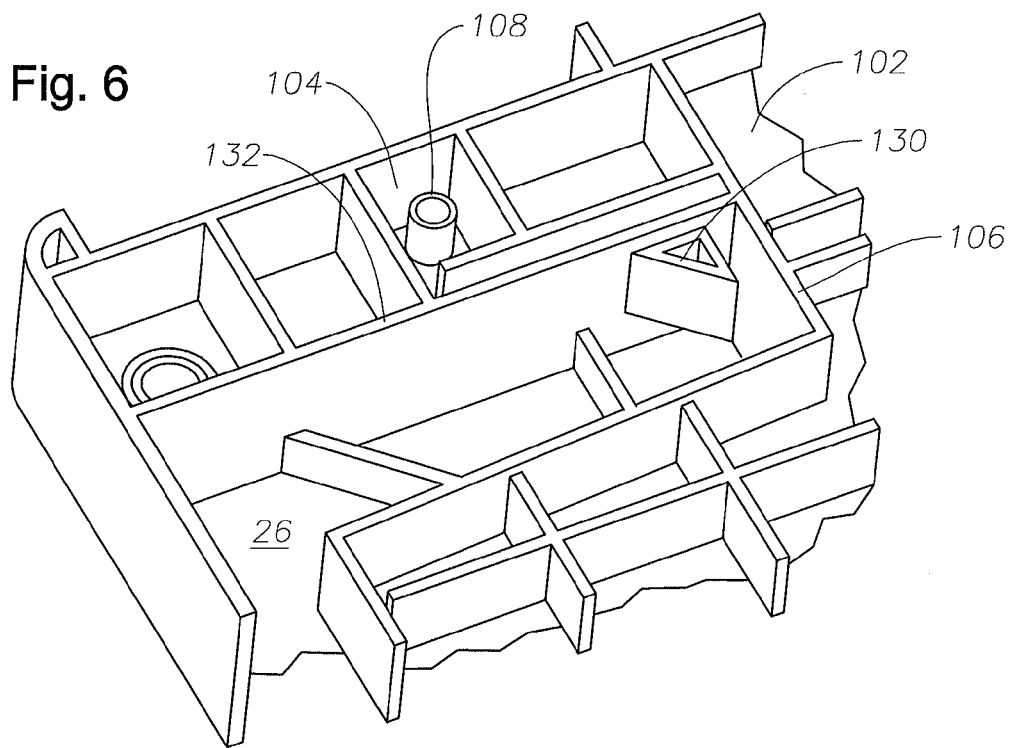
FIG. 6 is an enlarged, fragmentary, front, perspective view of body of a surgical cassette showing a bubble breaking structure according to a third preferred embodiment of the present invention.

FIG. 6 shows a bubble breaking structure 130 according to a third preferred embodiment of the present invention. Bubble breaking structure 130 is preferably an appendage extending from top internal surface 132 of aspiration chamber 26. Bubble breaking structure 130 preferably has a thin, planar geometry. The distal end of bubble breaking structure 130 is preferably angled downward toward the bottom of aspiration chamber 26. As bubbles or other entrained liquid pass near entry 106, they contact the internal surface of aspiration chamber 26 and/or bubble breaking structure 130. Such contact breaks the bubbles, and any entrained liquid falls back into aspiration chamber 26. The downward angling of structure 130 also prevents upward flow of liquid through entry 106.

The present invention is illustrated herein by example, and various modifications may be made by a person of ordinary skill in the art. For example, the surgical cassette of the present invention may include a first bubble breaking structure in the aspiration source chamber and a second bubble breaking structure in the aspiration chamber.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic surgical system, comprising:
   an ophthalmic surgical device for aspirating liquid infusion fluid and ophthalmic tissue from an eye, said ophthalmic surgical device having a first fluid line fluidly coupled thereto;
   a vacuum generator having a second fluid line fluidly coupled thereto; and
   an ophthalmic surgical cassette, comprising:
      an aspiration port fluidly coupled to said first fluid line;
      an aspiration chamber having said liquid infusion fluid disposed in a bottom portion of said chamber and air disposed in a top portion of said chamber;

a third fluid line having a first end and a second end, said first end of said third fluid line fluidly coupled to said aspiration port, and said second end of said third fluid line fluidly coupled to said aspiration chamber;

an aspiration source chamber fluidly coupled to said aspiration chamber via an entry and having a port disposed therein, said port fluidly coupled to said second fluid line so that during operation of said ophthalmic surgical system said vacuum generator creates a vacuum in said ophthalmic surgical device, said first fluid line, said third fluid line, said aspiration chamber, and said aspiration source chamber, and so that some of said liquid infusion fluid is entrained within air bubbles in said top portion of said aspiration chamber; and a bubble breaking structure disposed within said aspiration source chamber between said entry and said port, said bubble breaking structure having a geometry that facilitates breaking of said air bubbles so that said entrained liquid falls back into said aspiration chamber and does not pass to said vacuum generator, said geometry of said bubble breaking structure comprising:

a first appendage having a thin planar geometry, a proximal end beginning at an internal wall of said aspiration source chamber, and a distal end that is angled downward from said proximal end; and a second appendage disposed above and in a generally opposing manner relative to said first appendage, said second appendage having a thin planar geometry, a second proximal end beginning at said internal wall of said chamber, and a second distal end that is angled downward from said second proximal end.

* * * * *